United States Patent
Bateson et al.

(10) Patent No.: US 7,201,040 B2
(45) Date of Patent: Apr. 10, 2007

(54) RHEOMETER WITH AXIAL RESISTIVE FORCE MEASUREMENT

(75) Inventors: Ian David Bateson, Godalming (GB); Timothy Nicholas Raven, Godalming (GB); James Alfred Walker, Godalming (GB)

(73) Assignee: Stable Microsystems Limited, Godalming, Surrey (GB)

( * ) Notice: Subject to any disclaimer, the term of this patent is extended or adjusted under 35 U.S.C. 154(b) by 37 days.

(21) Appl. No.: 10/496,539

(22) PCT Filed: Nov. 28, 2002

(86) PCT No.: PCT/GB02/05357

§ 371 (c)(1),
(2), (4) Date: Nov. 5, 2004

(87) PCT Pub. No.: WO03/048743

PCT Pub. Date: Jun. 12, 2003

(65) Prior Publication Data

US 2006/0070428 A1    Apr. 6, 2006

(30) Foreign Application Priority Data

Nov. 28, 2001 (GB) .................................. 0128486.8

(51) Int. Cl.
*G01N 11/14* (2006.01)
(52) U.S. Cl. ............... 73/54.28; 73/54.23; 73/54.38
(58) Field of Classification Search ............ 73/54.01, 73/54.23, 54.28, 54.38
See application file for complete search history.

(56) References Cited

U.S. PATENT DOCUMENTS

| 5,610,325 | A | | 3/1997 | Rajagopal et al. |
| 6,065,330 | A | * | 5/2000 | Freeman et al. ............ 73/54.28 |
| 6,481,267 | B1 | * | 11/2002 | Iles et al. .................. 73/54.28 |

FOREIGN PATENT DOCUMENTS

| DE | 197 08 323 A1 | 9/1997 |
| EP | 0798 549 A2 | 10/1997 |
| EP | 1 102 053 A2 | 5/2001 |
| FR | 2 798 465 | 3/2001 |
| GB | 2289947 A | 12/1995 |
| WO | WO 90/08309 | 7/1990 |
| WO | WO 97/36162 | 10/1997 |

OTHER PUBLICATIONS

Chapter III, "Some Commercial Rotational Viscometers," Viscosity and Flow Measurement A Laboratory Handbook of Rheology by Van Wazer, et al., *Interscience Publishers*, 1963.

* cited by examiner

*Primary Examiner*—Daniel S. Larkin
(74) *Attorney, Agent, or Firm*—Hamilton, Brook, Smith & Reynolds, P.C.

(57) ABSTRACT

A rheometer comprises a vessel mounted on a stand and a rotatable blade mounted above the vessel. A substance for rheometric assessment is put in the vessel. The rotor is advanced linearly into the substance while at the same time rotating. The blade is arranged with a profile such that there is substantially zero slip as it progresses, thereby minimising disturbance to the substance. The rheometric assessment is based on the axial force exerted as a result of the resistance of the substance to the progression of the blade through it.

30 Claims, 7 Drawing Sheets

RHEOMETER WITH AXIAL RESISTIVE FORCE MEASUREMENT

RELATED APPLICATIONS

This application is the U.S. National Stage of International Application No. PCT/GB02/05357, filed 28 Nov. 2002, published in English, and claims priority under 35 U.S.C. § 119 or 365 to Great Britain Application No. 0128486.8, filed 28 Nov. 2001.

FIELD OF THE INVENTION

This invention relates to rheomtry and to rheometers for assessing rheometric characteristics of a substance.

BACKGROUND OF THE INVENTION

Various forms of rheometer are known which depend upon the determination of torque required to rotate a member through a body of material the rheometric characteristics of which are under investigation.

In effect, the torque is a measure of the resistance to the movement of the member presented by the substance. Examples of known rheometers are found in Chapter III 'Some Commercial Rotational Viscometers' of the book 'A Laboratory Handbook of Rheology' by Van Wazer et al., Interscience 1966 which is incorporated herein by reference. Such devices are used to gauge characteristics such as, for example, viscosity, flow, homogeneity, etc. The torque required to rotate the member through the substance is related to the resistance to movement presented by the substance itself. While the book is of a considerable age, it is still the case that its disclosures are broadly representative of the prior art in the field of rheometry today. Consistent among the teachings of the known devices is the use of a rotating member. However, because the characteristic movement of the member is rotary, it is cyclical. In certain circumstances the cyclical nature of the movement of the member means that it passes through a disturbed region of the substance after the first passage of the member. Thus, unless the substance is one which is able substantially fully to recover before the next disturbance by the member at the rate at which it is rotating, the torque required to drive the member will be different from cycle to cycle.

The book referred to above discloses a modification of the Brookfield Viscometer on page 144 in which the basic hand-held Brookfield instrument is mounted on a 'Helipath' stand above a vessel containing a substance under investigation. The mounting for the device on the stand is motor driven so that it can lower the viscometer at the same time as it is rotated. The member describes a helical path as it progresses. By virtue of this helical progression, the member encounters only undisturbed material as it rotates. As is stated in the book, the Helipath Brookfield Viscometer is used for material with high yield values or extreme thixotropic or rheopectic effects. In short, materials unable to recover due to the passage of a blade can more accurately be assessed for rheometric characteristics by a member describing a helical path through the material. In keeping with the rest of conventional rheometer practice, the rheometric characteristic is assessed by monitoring the torque required to rotate the member at a given rate.

A later example of a rheometer is disclosed in EP-A-0798549, which is incorporated herein by reference. In the disclosed device the member is again both rotated and driven linearly into the substance. While monitoring the axial forces produced is intended as an option, it is for controlled compression of the substance or for feedback in controlling the device. While powders are mentioned, it fails to distinguish between them, and liquids and viscous solids. The rheometric assessment of a characteristic of the substance only involves monitoring the torque in accordance with conventional practice. Thus, torque remains the recognised quantity by which rheometric assessment is carried out.

SUMMARY OF THE INVENTION

According to the present invention, there is provided a rheometer comprising: a vessel for a substance to be rheometrically assessed; a blade member; drive means for rotating and axially moving the blade member through the substance in the vessel; means for monitoring a parameter indicative of the axial resistive force of the substance to the passage of the member through the substance; and means for deriving a rheometric assessment of the substance from the monitored parameter.

It has been recognised by the inventors of the present invention that it is possible to derive usable rheometric readings from the measurement of axial force generated from a progression of the member through the substance, particularly a powder, and to ignore rotational forces. This is against decades of previous thinking which was based on deriving such readings from rotational forces. Furthermore, the monitoring of axial force is particularly straightforward, versatile and reliable in comparison with torque. Devices for measuring torque are more expensive than linear force transducers. Torque sensing devices are more difficult to install, set up and calibrate. Furthermore, torque sensing devices are less reliable in use and are prone to ingress by contaminants. As in conventional rheometers, the member in the present invention is also rotatable. However, the rheometric assessment is not based on sensing the rotary aspect of the motion in the present invention.

By sensing axial force, or a parameter indicative of it, and the distance travelled, the work done can be assessed. Such axial monitoring can be carried out in one direction or both. The distance can be a set distance within the substance or a distance between an upper surface of the substance and a preferred lower position.

The member is preferably mounted on a shaft or spindle and may be driven by one or mote suitable electric motors, such as a stepper motor, to provide the degree of control and resolution over its axial movement and, when applicable, its rotary motion.

The member is desirably a multi-bladed device, but could be single bladed, having a blade or blades extending outwardly from the axis of the member. It is found that a particularly suitable member has a blade or blades which have surfaces defining an aspect ratio, and which are arranged, so that leading and trailing edges, in relation to the movement of the member, are defined along the substantially axial path. For example, a propeller form for the blade could be used. This has a particularly advantageous construction. The speed of progression and rotation of the member can be set such that the blade progresses through the material with substantially zero slip, thereby minimising the disturbance to the substance in the vessel.

The means for monitoring may be a load cell, such as a strain gauge, attached to the rheometer in order for the axial force arising from the progression of the member through the substance to be sensed. The load cell may be arranged in a support for the vessel, thereby sensing the force transmitted through a substance to the vessel. Alternatively, the load cell may be arranged in relation to the drive means to sense the reactive force transmitted from the substance through the member.

Other means for monitoring a parameter indicative of the axial force may derive an indication from the drive means of the work done in moving the member. For example, when the drive means is an electric motor the work done can be derived from the current by means of a current sensing device in the electrical supply to the motor. The movements (e.g. revolutions or part revolutions) of the drive means may be monitored to provide additional data for analysis.

By monitoring a parameter indicative of axial force it is possible to carry out a first movement of the blade member through the substance until a predetermined load is reached and then to carry out a Theological assessment, or an additional one, at that point. Rheological assessment can be carried out on both the forward and reverse axial movements of the blade.

The invention also extends to a method of rheometric analysis of a substance comprising: preparing a substance for analysis in a vessel; rotating and axially driving a blade member through the substance to shear it; monitoring a parameter indicative of the axial resistive force of the substance to movement of the member through the substance; and deriving a rheometric assessment of the substance from the monitored parameter.

BRIEF DESCRIPTION OF THE DRAWING FIGURES

The present invention can be put into practice in various ways, some of which will now be described by way of example with reference to the accompanying drawings in which.

DETAILED DESCRIPTION OF THE PREFERRED EMBODIMENTS

Figure 1:
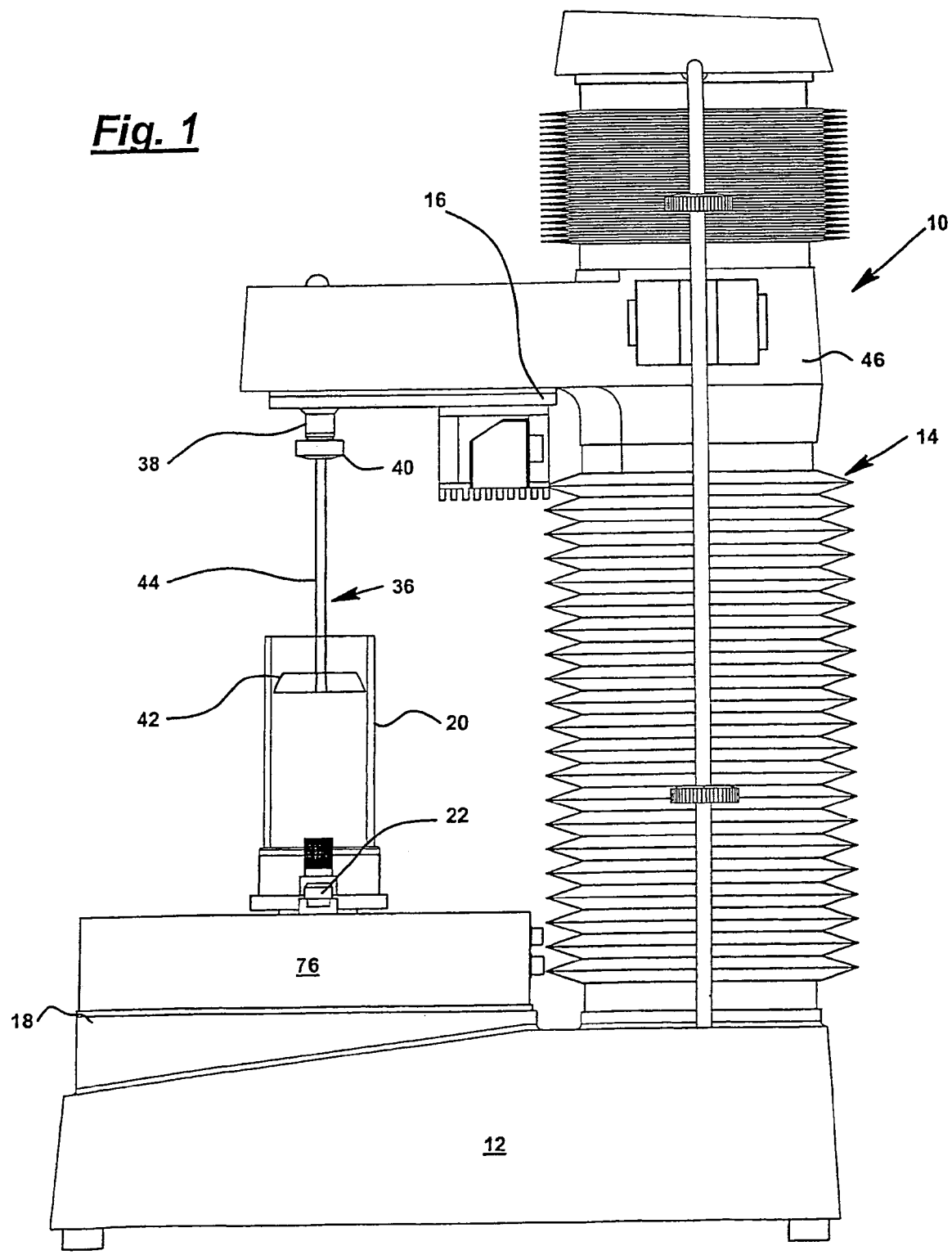
FIG. 1 is a general section of a rheometer according to an embodiment of the invention.
Figure 2:
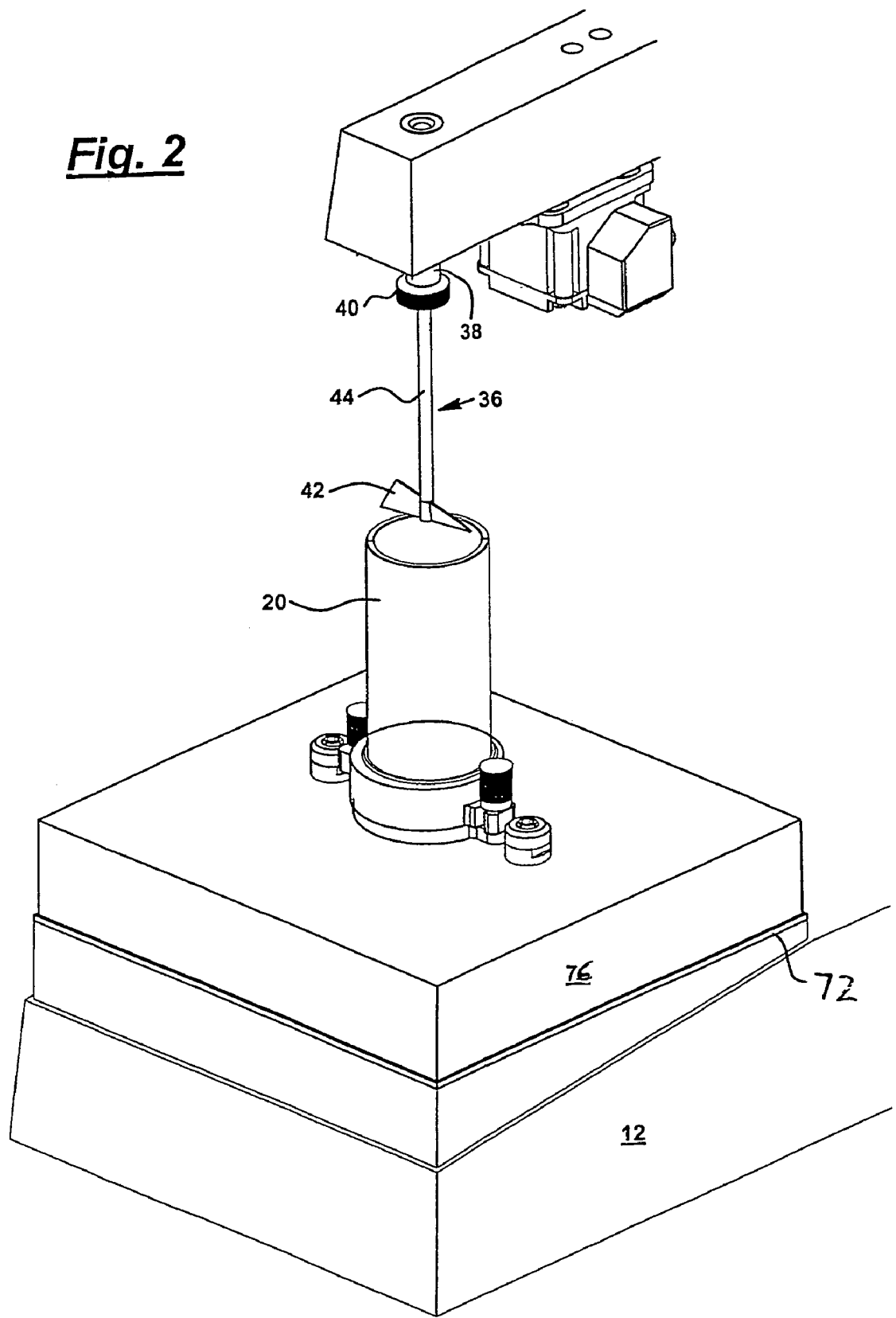
FIG. 2 is a partial view of the rheometer of FIG. 1.

Referring to FIGS. 1 and 2, one embodiment of a rheometer has a frame 10 comprising a foot 12, an upright 14 extending from the rear of the foot 12 and a gantry 16 extending from the upright over the foot 12. A platform part 18 is formed on the foot 12 supporting a test vessel 20 in a collar 22 mounted above the platform 18 on the sensing head of a load cell (to be described). The vessel in this embodiment has a 50 mm internal diameter and can hold a sample of 140 ml, approximately 70 mm in height. Other vessel sizes and suitably fitting blades can be used.

Figure 3:
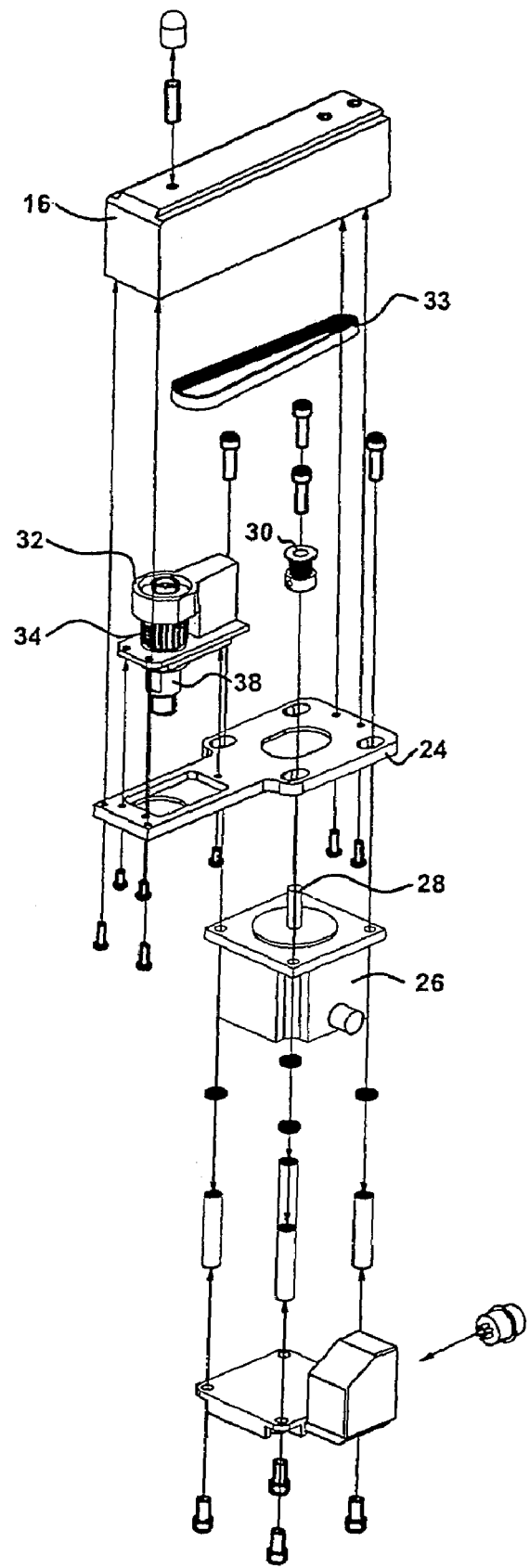
FIG. 3 is an exploded view of the gantry of the rheometer.

In FIG. 3, the arm 16 comprises a base plate 24 to which is mounted a rotation drive motor 26 having a drive shaft 28 carrying a gear wheel 30 and extending up through the base plate 24. A bearing assembly 32 is mounted on top of the plate 24 above the vessel 20. A toothed fabric/rubber timing belt 33 drivingly connects the gear wheel 30 attached to the drive shaft 28 of the motor to an input gear 34 of the bearing assembly 32.

Figure 6:
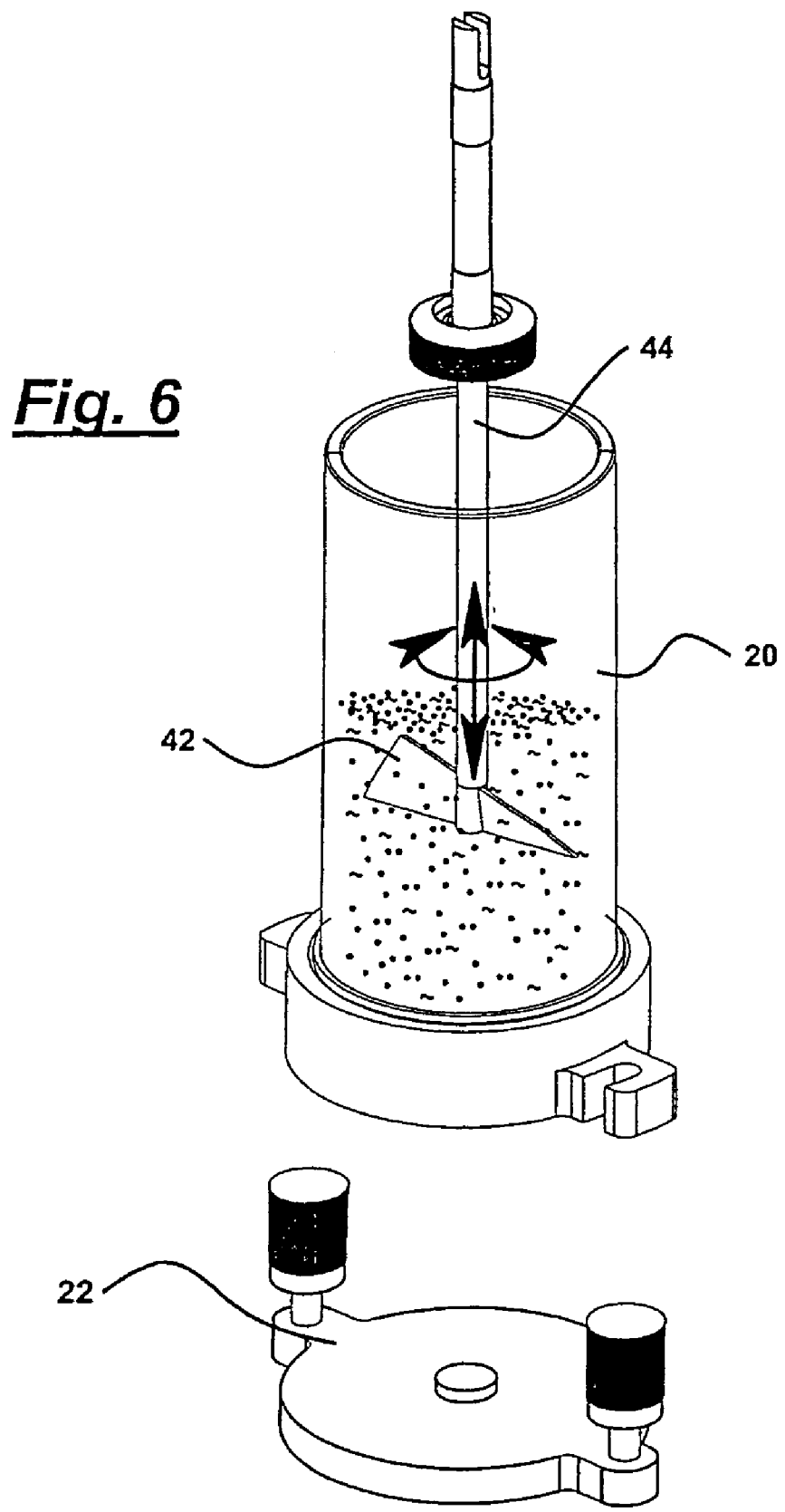
FIG. 6 is detail of a vessel and blade of the rheometer.

A rotor member 36 is secured to the output 38 of the bearing assembly 32 by a threaded retaining collar 40. As best seen in FIG. 6, the rotor member 36 has a propeller-type blade 42 at the end of a vertical shaft 44 which is positioned with its axis above the centre of the circular vessel 20. The propeller blade can be rotated in other ways. The rubber timing-type belt 33 is found to provide a particularly smooth and reliable form of transmission.

Figure 4:
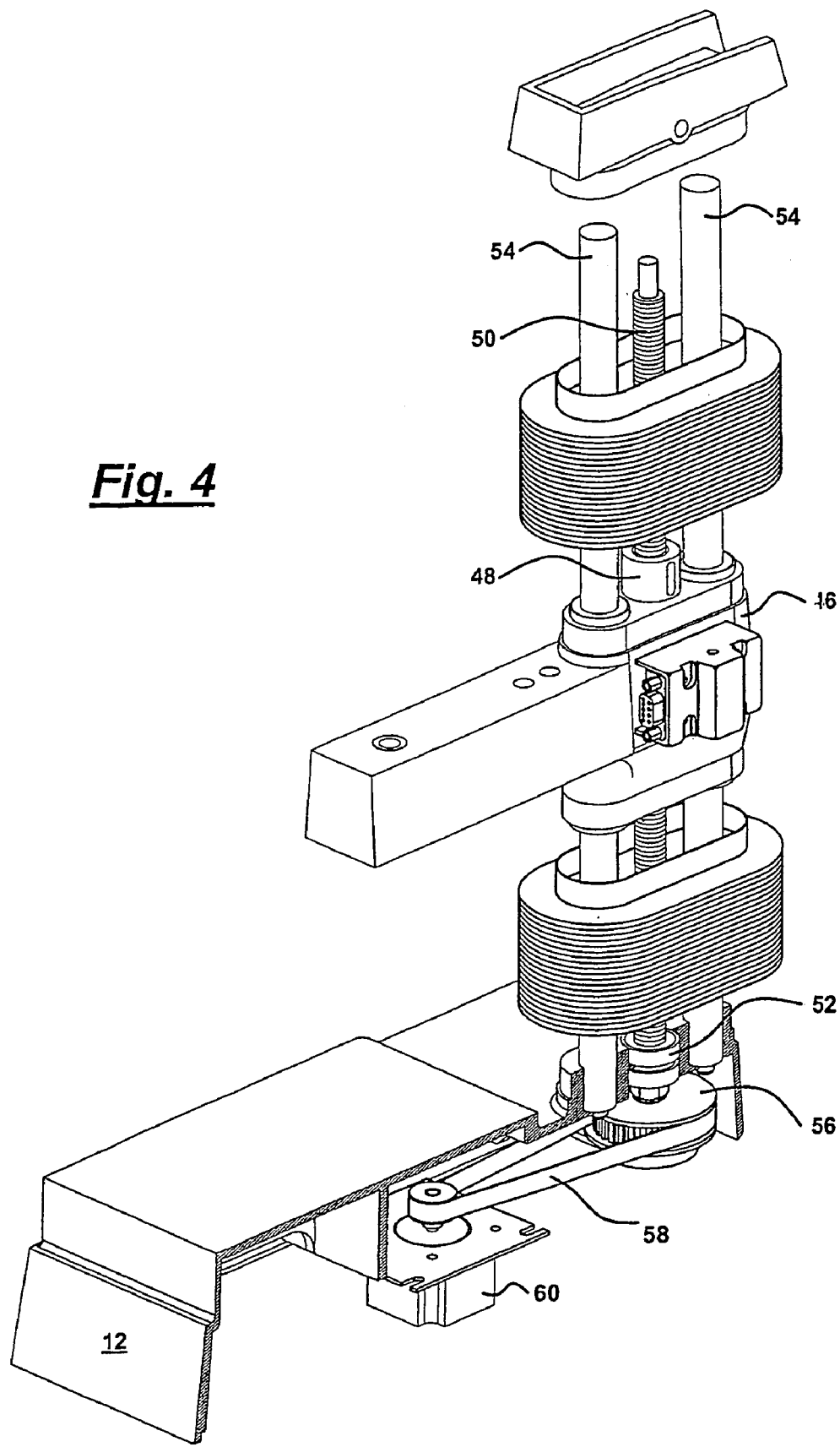
FIG. 4 is an exploded view of a gantry part of the rheometer.

Referring also to FIG. 4, the gantry 16 is mounted for linear movement above the vessel 20. A threaded attachment 48 is secured to the gantry 16. The attachment 48 is engaged with a thread of a vertical drive rod 50 passing through the gantry 16. The rod 50 is mounted in upper and lower bearings 52 in the frame 10 between front and rear vertical supporting stanchions 54 on which the gantry 46 rides vertically. Beneath a lower bearing 52, the drive rod 50 is fitted with a drive wheel 56. A further timing belt 58 transmits rotation from a further stepper motor 60 to the drive wheel 56. As the rod 50 is rotated, the gantry 16 rides linearly along the thread, guided between the vertical stanchions 54.

Figure 5:
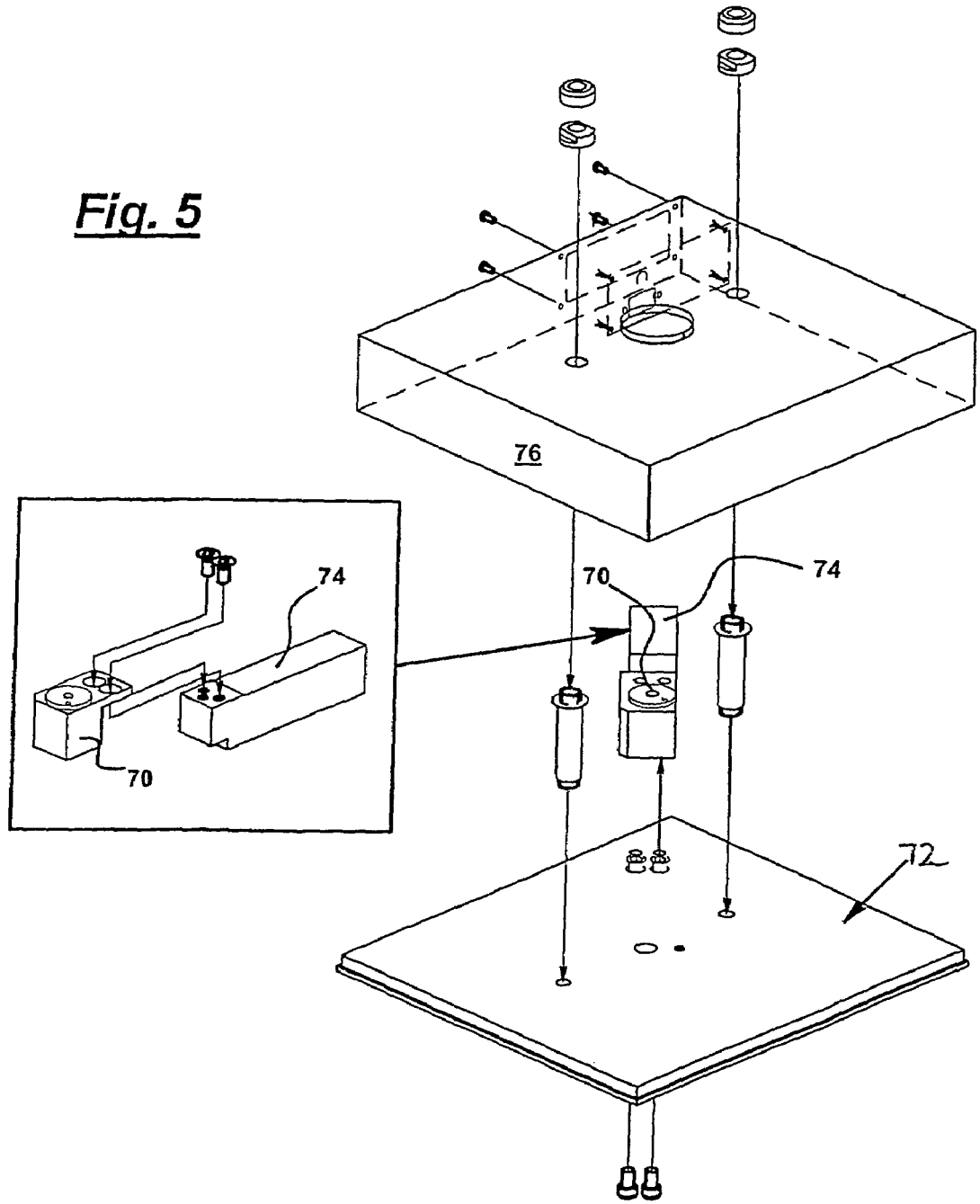
FIG. 5 is an exploded view of the base of the rheometer.

Referring to FIG. 5, to monitor the axial resistance of a substance to the movement of the blade 42 through it, a load cell 74 is mounted on a base portion 72 on the platform 18. The load cell 74 extends from the edge of the base into the centre and beneath an upper cover 76 mounted on the base portion 72. A mounting adaptor 70 protrudes through a central aperture in the cover 76, supporting the collar 22 holding the vessel 20 (see FIG. 1). The collar 22 is bolted to the mounting adaptor 70 to keep it in place. The load cell is bolted to the base 72. In this arrangement the load cell senses only axial forces exerted on it from the vessel 20. The output (not shown) of the load cell 74 is an electrical signal which is connected to electronic circuitry (not shown) in the foot of the apparatus. The electronics conditions the output of the load cell for subsequent output to a processing device, such as a personal computer (PC). This is described in further detail below. The data is analysed by the PC as necessary to provide quantitative rheometric results based on the force sensed by the load cell as a result of the progression of the rotor member 36 through the substance in the vessel. The load cell in this embodiment is a wire strain gauge-based device well known to the skilled person. Other devices could be used, such as a semiconductor-based strain gauge or a linear variable differential transformer (LVDT), to sense the axial force.

Figure 7:
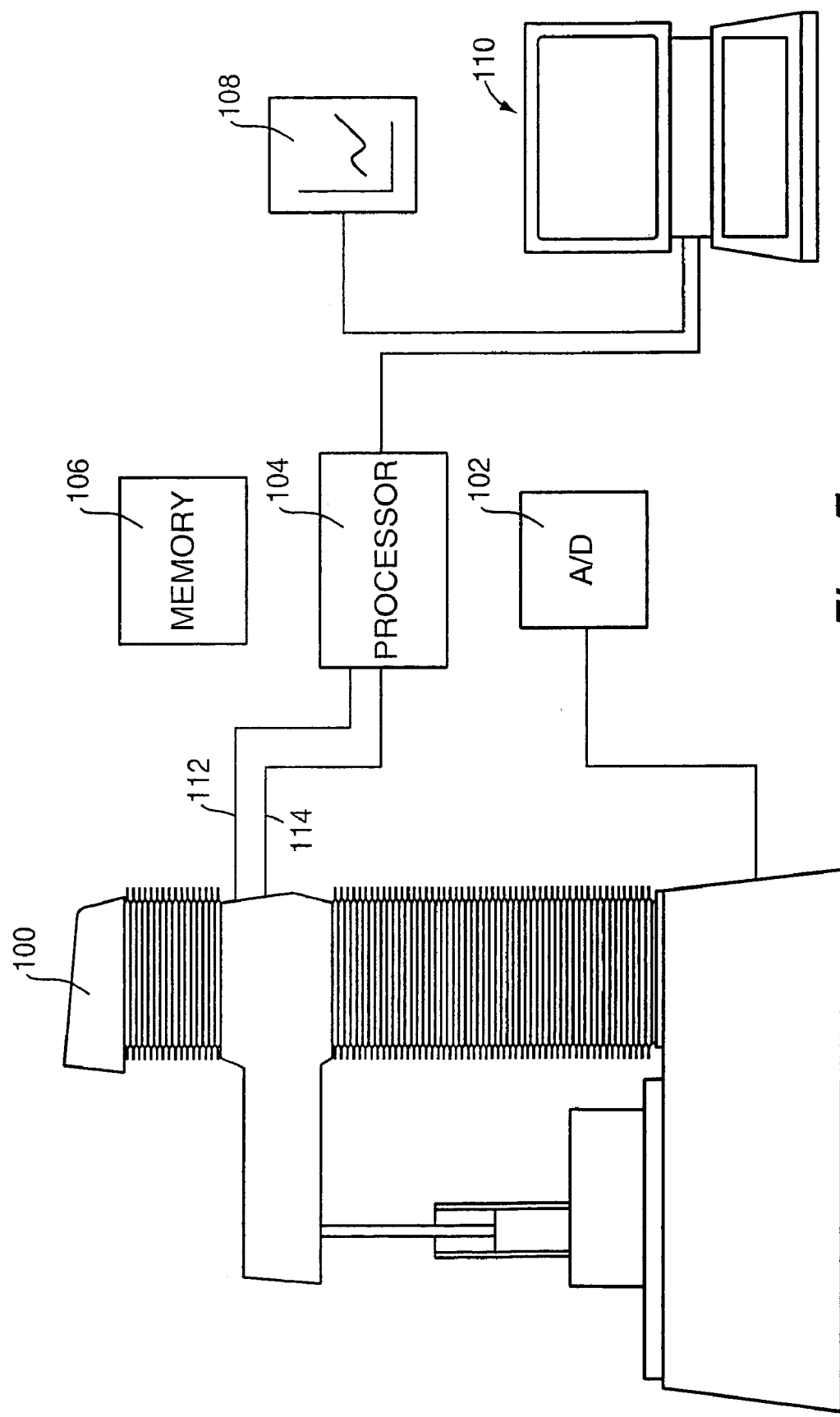
FIG. 7 is a schematic diagram of a system for rheometric assessment incorporating the rheometer of FIG. 1.

FIG. 7 shows a rheometer system comprising a rheometer 100 as described and an analogue-to-digital converter 102 which is supplied with the analogue output from the load cell 74. The digitised load cell information from the converter 102 is fed to a processor 104 which is conventional in construction and arrangement, having a memory 106 and an output connected to a plotter 108. An input/output user interface 110 is provided in the form of a keyboard/monitor or PC. Data captured in tests carried out by the system can be displayed on the monitor in numerical or graphical form according to known techniques. The processor 104 is programmed to control the motors driving the blade linearly and angularly, and to capture data at specified periods over specific points in the test cycle. For control purposes based on the axial force applied feedback according to conventional techniques can be derived from the output of the analog-to-digital converter 102. Motor parameter feedback and control signals to the motors for axial and angular movements of the blade are transmitted on lines 112 and 114, respectively.

The apparatus can be operated in various ways and the electronics, by which the motors are also controlled, is programmed automatically to effect a sequence of operations according to the manner in which it is required to be operated. The programming is conventional. The novel sequence of actions for rheometric assessment are described below.

The primary operation is to arrange the blade 42 above the vessel containing the substance to be analysed and for it to be lowered and raised in the substance at a predetermined rate by actuation of the motor 60 and at a rate of rotation caused by actuation of the motor 26, under the pre-programmed control of the processor 104.

The blade 42 on the rotor member has a propeller profile that increases in pitch angle with respect to the axis of rotation of the blade with increasing radial distance from the axis. Such a profile has a 'constant lead' so that it can effect as clean an entry into the substance as possible. Such profiles for propellers, by which the shearing of the substance is caused and turbulence is minimised, are well-known to the skilled person. The travel of a propeller blade following such a helical path is thus made up of simultaneous axial and radial progressions. These rates of axial progress and rotation can be such that the rotor blade enters and progresses through the substance at a rate of zero slip, but the blade may also be moved such that it progresses at an axial and radial rate that is greater or less than the helix angle possessed by the blade by virtue of its overall pitch. Under these conditions a variable axial force is imparted to the substance. In addition any such helical path may be progressed either downwards or upwards. This axial resistance to the passage of the blade following such a helical path is sensed as a strain on the load cell from which readings relating to viscosity in a liquid or, more generally flow characteristics, can be derived.

Once introduced into the substance in the vessel the test can take place at any desired depth. The blade is advanced to the appropriate position. The test itself consists of combinations of simultaneous or separate angular and axial movements that may combine to be a helical path or not. The reaction to these movements is the axial force that is sensed. The Theological or flow properties can, thus, be assessed. The degree of flow is related to the inverse of the force sensed. Varying the 'slip' (i.e. the difference between rate of axial progress of a given propeller type blade at a given rate of rotation) can be used in the assessment of the rheological properties of the substance. The controlling processor 104 can be programmed to carry out the desired functions in conventional manner.

The apparatus is of use in determining readings of viscosity in liquids and thixotropic materials. However, the invention is also of particular use in the pharmaceutical and other industries in which the rheometric (for example, flow) characteristics of powders have to be assessed.

The apparatus may be programmed so that the blade is rotated in the opposite direction to the helix, determined by the blade pitch. This alternative helix may be in the equal and opposite sense to the design helix of the blade pitch. The action of progressing such a helix would be to compress the substance as it travels into the vessel or lift up (aerate) the substance as the blade travels upwards out of the vessel. The reaction to these movements is also to produce axial force, which can be measured by a suitable transducer. This data can also be used to determine the Theological properties of the substance. Further rheological properties of the substance can be investigated by rotating the blade more quickly or more slowly, to realise a situation of negative or positive slip, about this opposite helix.

It has been found useful to describe the blade movements in terms of a vector, where the angle of this vector starts at 0°, which would describe a clockwise motion but no axial movement and 90°, would describe axial movement but no rotation. All the angles between these two values would include both movements, the rotational movement being in proportion to the cosine of the angle and the axial movement proportional to the sine of the angle. Angles beyond 90°, and up to 180°, would follow the same rules but the rotation would be in the anticlockwise direction. This method is well known in mathematics. The direction of the axial movement is stated as being upwards or downwards in all cases. Thus the full range of possible movements can be described simply by stating an angle in degrees, an axial direction and lastly the desired speed of travel, or magnitude of the vector in terms of millimetres per second. All these parameters refer to the tip of the blade, the processor is informed as to which blade is fitted and is programmed to determine the relevant rotational and axial parameters required for control by virtue of its programming.

Linear speed and rotational speed are not input by the user at the keyboard 110. Instead, the user is able to specify the blade type, blade tip speed and angle from which the processor 104 then calculates the linear and rotational speeds.

In all that follows a blade with a left-handed helix, or in more simple terms, thread, is used. Where angles and speeds are mentioned, these are merely to illustrate a method and may in practice vary widely from these values, as indeed may the movements and the order of movements to suit the requirements of the experimenter or the substance being tested.

Although not shown in the drawings, the blade may usefully have a profiled boss at its centre further to reduce the disturbance caused to the substance as the blade passes through it.

When the blade is moving downwards into the base of the vessel, compaction of the powder below the blade occurs when the blade is rotating in a clockwise direction. Compaction occurs until the specified test progression angle reaches 90° at which the blade ceases to rotate, beyond 90° the blade begins to rotate anticlockwise and the blade action is generally said to be 'slicing' including the special case of moving through the substance with zero slip. Maximum compaction of a powder should occur when the face of the blade is impacting the powder normal to its progression angle, in the case of a rotor with a 135° angle this occurs at a progression angle of 45° in the downwards direction.

When the blade is moving upwards within the vessel, lift displacement, or aeration, of the powder below the blade occurs when the blade path is moving in an anticlockwise direction. Aeration occurs at angles greater than 90°, at angles below this the blade is said to be slicing. This rotational and vertical motion of the blade is seen to lift the sample on the face of the blade. As upward movement continues through the sampled column, the sample falls over the blade, hence providing aeration. With many powders this displacement mode aerates successive powder test samples in a uniform manner, removing operator dependence, for satisfactory sampling.

The rotational direction is chosen according to the required testing effect on the sample and is specified by the angle. If a clockwise rotation is required an angle between 1° and 90° is specified. If an anticlockwise rotation is required an angle between 90° and 180° is specified.

Powders often have characteristics which are significantly different from both liquids and viscous solids to which the majority of rheometric assessment techniques have been applied, and from which those techniques have all been developed. However, for powders it is found that other considerations apply, such as caking and interparticle friction. Caking is the tendency of a powder to aglomerate or form lumps (cakes) during storage or transportation. Interparticle friction, powder cohesion and flow stability are all parameters used to describe the properties of a powder under the conditions of flow. Interparticle friction may change as a powder flow rate changes. Thus, information on interparticle friction, or information indicative of it, is very useful in process management in a production facility, quality control and material development.

By these movements described above the substance can be disturbed on purpose to agitate (aerate or mix) it in the vessel prior to a rheometric reading being made. The purpose of which would be to ensure that prior to the start of any test the substance would be in a known and repeatable state and not dependant on the manner in which an operator filled the vessel. Such pre-conditioning by compressing or aerating the substance is particularly useful in powder applications in, for example, the pharmaceutical industry.

The apparatus can be pre-programmed to condition the powder column in the vessel 20. This may be done by rotating the blade 42 in an anti clockwise direction but with only a small amount of axial speed. The downwards action is performed at a tip speed of 50 mm/s and an angle of 175°, and upwards action is performed at a tip speed of 50 mm/s and an angle of 178°. This movement is usually performed twice over the entire height of the powder column, which in practice has been found enough to pre-condition any powder column. The action performed by these movements lifts the powder slightly throughout the column aerating the powder, whilst at the same time breaking up any agglomerations and then allowing the powder to fall gently over the top edge of the blade and come to rest behind it.

A succession of upward and downward passes of the blade (for example two down and two up) according to a conditioning phase of a test creates a uniform packing density in the powder, i.e. it is free from distortions which may otherwise be present due, for example, to the method of-filling the vessel 20 with the powder under test, or settlement of the powder prior to testing. While the initial conditioning movement of the blade is usually downwards, some tests may require the conditioning to start in the opposition direction from within the powder, thereby requiring a reversal of the sequence.

As referred to above, caking is the rheometric property of a powder that is often of interest. The conditioning in which the blade is reversed into the powder can be used to compact it into the base of the vessel to a predetermined force value. Then the blade is programmed to move forwards, slicing up through the compacted material with zero slip, causing minimal disturbance to the sample in the process. This sequence of compacting and slicing up through the material can be repeated a number of times. The sequence progressively compacts the powder in the base of the vessel to homogenise it.

It is often of commercial interest to analyse the data in a way which gives information on the rate at which the cake is formed. This is monitored by sensing the axial force on the vessel as compaction takes place in each cycle. At a given value of sensed force, corresponding to a desired level of compaction, the blade is then programmed to slice through the material to provide a reading of the resistance of the material to axial movement of the blade. This output is indicative of the cohesion of the powder in the compacted state.

The tests are carried out according to a macro written for the processor. These are selectable by the user through the keyboard. The first is indicative of the rate at which the cake is formed. In all cases speeds, angles, directions, both upwards and downwards, target forces and target distances can be varied by the user.

After the pre-test conditioning described above, the top surface of the column of powder in the vessel may be uneven. To address this the rotor is moved according to its compacting motion (i.e. clockwise for the embodiment in FIGS. 1 and 2) towards the surface of the sample at a tip speed of 20 mm/s and at a rate of rotation equivalent to an entry angle of 2° for the blade. This gradual and gentle progression towards the powder smoothes the top of the sample. When the strain gauge transmits a signal indicative of a 5 g force exerted on the sample by the blade, the smoothing process is stopped. This procedure also allows the system to record the column height during the caking test. This gives data on the extent to which the powder settles in storage.

When the force exerted reaches the target value of 5 g as above, sample testing continues with the recording of data as the blade moves down through the powder at a tip speed of 20 mm/s and an angle of progression of 20°. The compaction which takes place by virtue of this movement of the blade is programmed to stop when the strain gauge signal indicates a target force on the sample of 1 kg. At this point the rotor returns up through the sample at a speed of 10 mm/s and an angle of progression of 45°. This angle equates to a rate of progression giving zero slip, as the blade angle is also 45°, an angle of 45° in the upward direction being equivalent to one of 135° in the downward direction. This means that the blade cuts through the powder like a knife, creating minimal disturbance as it does so. This is repeated for five compactions and four returns. At the end of the fifth compaction, the blade is programmed to slice through the compacted powder of the sample at an angle of progression of 175° in sympathy with the blade pitch. As the blade moves, the axial force required to do so is recorded from the beginning of movement to the end. Finally, the blade is returned back up through the sample and out of it and a tip speed of 100 mm/s and an angle of 175°.

From these test movements the macro records:
- the height of the column at the start of each compaction cycle—as determined by the blade exerting 5 g of force on the sample
- the distance travelled when the 'end force' of 1 kg is reached—this is the cake height for each cycle
- the mean force and work carried out (g.mm) to slice through the caked (compacted) sample after the five compaction cycles.

The data is applied to a spread sheet in which volume and cake height ratios are set out against material column height. Similarly, the cake strength is set out in the spreadsheet as mean axial force and the work done (the area under the force/distance graph for the travel of the blade through the sample).

Another form of analysis is aimed at measuring several parameters during one test sequence, these are; the interparticle friction and its change as flow rate changes, powder cohesion and flow stability. This latter is essentially an assessment of change in flow characteristics due, for example, to attrition effects. These properties are assessed during the powder flow speed dependent test. This information is important for:

process modification—if a product manager needs to increase production rates, it is necessary to know how the powder which is a constituent of the production process will behave at a changed level of throughput
    quality control—manufacturers and customers need to analyse samples for batch consistency
    process monitoring
    ingredient modification The test for powder flow speed dependence comprises a sequence of two conditioning cycles to induce homogeneity in the sample. The rotor is moved down through the sample at a speed of 50 mm/s at an angle of 175°. Each cycle is then completed with an upward movement through the sample at a speed of 50 mm/s and an angle of 178°.

The testing phase comprises a number at sets of differing speeds, of two cycles each. The first set of two cycles is as follows:

The rotor is programmed to move down through the powder column at a tip speed of 10 mm/s and an angle of 5°, compacting the powder in the column. While doing this, the system is capturing data on force, axial distance, and time. This data corresponds to the resistance of the powder to being pushed at a controlled flow rate, i.e. the interparticle friction of the powder. At the bottom of the powder column the rotor is programmed to slice through the powder at near zero axial speed and not to measure data, this serves the purpose of stopping any hard compacted layer building up. The rotor is then programmed to move up through the powder at a tip speed of 50 mm/s and at an angle of 178°. Again, the data is being recorded. This data corresponds to an indication of the cohesion of the powder.

Once these two cycles are complete, the next two cycles commence immediately in the same format, but with a downward compaction blade speed of 20 mm/s. At the end of these two cycles the compaction speed is changed to 50 mm/s, then a further two cycles at a compaction speed of 100 mm/s, followed finally by two cycles at 10 mm/s. Data on force, distance and time is recorded as before.

Using the macro on the system, the positive and negative areas of force and distance for the down and up strokes of the blade through the sample, respectively are recorded and inserted into a result spreadsheet. The spreadsheet is set up to average the two areas for the compaction data (as the blade moves down through the powder column) at each rate of blade travel. These are recorded as the compaction coefficient at 10, 20, 50 and 100 mm/s. The cohesion (as the rotor moves up through the powder and lifts and separates the compacted powder) is also recorded from the first two cycles and averaged. The compaction coefficient for the final two cycles at 10 mm/s is averaged and the ratio for that average with the average from the initial two cycles at 10 mm/s is derived to assess whether the powder has broken down during the testing. This is shown in the results spreadsheet as Flow Stability. A figure of flow stability close to 1.00 means it has not changed at all during the testing. If the figure is greater than 1.00, it is an indication that the sample has changed during testing (giving a higher compaction coefficient). If it is less than 1.00 the sample has changed to give a lower compaction coefficient.

If the flow stability is close to 1.00 and the compaction coefficient is increased at higher flow rates, the product is more resistant to flow at higher flow rates (and may result in underfilling in a production environment). If the flow stability is close to 1.00 and the compaction coefficient is decreasing at higher flow rates, than this shows that the product is less resistant to flow (it flows more easily) at higher flow rates. This can be used to avoid overfilling in a production environment. If the flow stability is different to 1.00 then it shows that the product may be liable to attrition during processing or transportation which can be investigated further using a texture analyser to carry out a compaction test on the powder or granules and assess the force to fracture the product, and also to test its elasticity characteristics.

In an alternative test, the substance may be compacted to a specified substantially constant strain. The machine has the ability to measure the height of the column prior to compaction (as described above). Thus it is able to then determine how far into the vessel the rotor must be inserted to create a specified degree of strain. Strain in this context is defined as 'change of length' divided by 'original length' of the column of substance in the vessel. The rotary motion required to maintain the helical progression under these circumstances may be determined by the user or not used at all. Data collection during this operational mode is optional. This mode of operation could be terminated by the elapse of a specified time or a force reading being exceeded.

As a further alternative, the substance may be compacted (or aerated) under conditions of constant force. In this mode a maximum speed may be specified at which the rotor will penetrate the substance. When a specified force is reached, instead of stopping or performing another action/movement, the rotor continues to move but at a new rate determined solely by the requirement to continue to exert the specified force upon the substance. The control of the rate is by conventional feedback of the strain gange output to the motor control. The rotary motion required to maintain the helical progression under these circumstances may be used or not as determined by the user. Data collection during this operational mode is optional. This mode of operation could be terminated by the elapse of time or distance travelled.

By limiting the device to the sensing of axial forces the implementation of a rheometer is simplified. Because rheometers are often used in contaminating environments in which the ingress of dust and/or moisture, etc. is a problem, avoiding having to sense the force due to relative rotation of parts is of advantage. Furthermore, devices used to sense linear forces are more easily set up and more reliable and versatile than devices used to sense torque.

The comprehensive software provided with the powder flow analyser of the present invention allows almost any feature of a data characteristic to be recognised and recorded, including peaks, intermediate threshold peaks, gradients, elapsed time and distance events, smooth and jagged line comparisons, and many other features. In addition analytical macros for the data analysis can be written to suit a particular test event or amplify a special characteristic of the samples. The data gathered includes the axial distance travelled, time elapsed and axial force exerted. Generally, for a particular powder the force/work done both downward (compaction) and upwards (aeration) provide highly repeatable measurements. For these to be made the subject of comparison between samples, the starting height (or volume) of the samples within the test vessels must be the same after initial conditioning by the analyser.

It will be appreciated that the data gathered by the rotor with the blade traversing the sample vessel contents is analysed by computing the axial work done (axial force multiplied by the axial distance travelled) for a number of different fill levels of the sample tube. This data is gathered separately for the upward and downward movements and then plotted on a graph as work done on the Y axis versus sample volume on the X axis. The relationship demonstrated by this technique shows that the work done increases with increasing sample volume according to an exponential function. However, the exponential magnitude of this curve function is so slight that it can be considered linear for the fill volumes in use at present (i.e. between 120 and 180 ml for a 50 mm internal diameter vessel). This finding is important since it makes comparisons between samples of the same product by using different volumes possible. In the pharmaceutical industry there are sometimes only very small quantities available and, in addition to this, samples may be prepared in several locations by different operators.

The measurement of axial force alone in rheometric assessment is unique to the present invention. Historically, rheometers have assessed torque as the associated rotational movement can be carried out indefinitely, not relying on the length of a test bed or depth of vessel, nor any other physical limitation. The mechanical measurement method as used in the past required measurement of the forces in steady state due to the repeated nature of the rotation cycle. However, according to the invention the movement of the blade in the helical form, rotated at a given speed, imparts thrust to the sample. Therefore, the ability of the product to 'flow' can be measured by simply measuring the axial force. The 'flow' of any one product type will also depend on the density, and in the case of a powder, the packing density. It is not necessary to measure the input torque. This will vary with product type but is not as sensitive a measure as axial force. By moving the rotor axially simultaneous with the rotor linear motion, the action of the rotor can be a compressive or a lifting one. When the actions are used in conjunction with a selectable data capture system, a powerful analytical tool is provided.

It will be apparent to the person of ordinary skill in the art that various modifications and variations can be made to the present invention. For example, a toothed timing belt is illustrated in the specific embodiment, whereas the motor may be arranged to drive the rotor member in rotation directly or through other forms of transmission. The rotor member may also be moved linearly other than by a helical screw, such as by belts, or the use of a direct drive from a linear motor. The relative movement between the blade and vessel could equally well be achieved by motion of the vessel. Additionally, while the load cell is arranged to sense forces transmitted through the vessel, it could equally well be arranged to sense forces transmitted through the rotor member along the shaft above the vessel. Similarly, readings of the resistance to the movement of the rotor member through the substance can be derived from the power consumed by the motor driving the member linearly. For example, current supplied to the motor could be monitored. The blade is described as being of the propeller type in profile so that it can be used in a way in which the least disturbance is created as the substance is sheared by the blade's leading edge. However, coarser blade or non-propeller-type profiles could be used. Thus, the skilled person will appreciate that variation of the disclosed arrangements are possible without departing from the invention. Accordingly, the above description of an embodiment and its variants is made by way of example and not for the purposes of limitation. The present invention is intended to be limited only by the spirit and scope of the following claims.

What is claimed is:

1. A rheometer comprising:
   a vessel for a substance to be rheometrically assessed;
   a blade member;
   drive means for rotating and axially moving the blade member through the substance in the vessel;
   means for monitoring a parameter indicative of the axial resistive force alone of the substance to the passage of the member through the substance; and
   means for deriving a rheometric assessment of the substance only from parameters monitored in the axial direction of the blade member.

2. A rheometer as claimed in claim 1 in which the parameter is monitored in opposite directions of passage of the member through the substance.

3. A rheometer as claimed in claim 1 in which the means for deriving include means for calculating the work done in axially moving the member.

4. A rheometer as claimed in claim 3, including means for measuring axial distance travelled by the member while the parameter is monitored.

5. A rheometer as claimed in claim 1 in which the means for monitoring include means for sensing the force exerted resulting from resistance of the substance to movement of the member.

6. A rheometer as claimed in claim 5 in which the means for sensing the force include a load cell arranged to sense the axial force transmitted through the vessel.

7. A rheometer as claimed in claim 6, including a base on which the vessel is mounted, and in relation to which the load cell is mounted to sense the axial force transmitted through the vessel.

8. A rheometer as claimed in claim 5, including a frame supporting the blade member, the means for sensing the force being arranged in relation to the frame to sense the axial force transmitted through the member.

9. A rheometer as claimed in claim 1 in which the drive means include an electric motor arranged to drive one of the blade member and the vessel to achieve relative motion between them, the means for monitoring include current sensing means arranged to monitor the current drawn by the motor.

10. A rheometer as claimed in claim 1 in which the blade member comprises a shaft having at least one radially extending blade arranged towards one end.

11. A rheometer as claimed in claim 10 in which the or each blade has a propeller profile with increasing pitch angle with respect to the axial direction with increasing radial distance from the shaft.

12. A rheometer as claimed in claim 11 in which the drive means are operable to drive the at least one blade for substantially zero slip.

13. A rheometer as claimed in claim 12 in which the drive means are operable to drive the at least one blade in the opposite direction to that dictated by the pitch angle.

14. A method of rheometric analysis of a substance comprising:
   preparing a substance for analysis in a vessel;
   rotating and axially driving a blade member through the substance to shear it;
   monitoring a parameter indicative of the axial resistive force alone of the substance to movement of the member through the substance; and
   deriving a rheometric assessment of the substance only from parameters monitored in the axial direction of the blade member.

15. A method as claimed in claim 14 in which the parameter is monitored in opposite directions of passage of the member through the substance.

16. A method as claimed in claim 14 including calculating the work done in axially moving the member.

17. A method as claimed in claim 16 including measuring an axial distance travelled by the member while the parameter is monitored.

18. A method as claimed in claim 14 in which the monitoring includes sensing the axial force exerted by the resistance of the substance to the passage of the member.

19. A method as claimed in claim 14 in which an electric motor is arranged to move the member relative to the vessel, the monitoring including sensing the current drawn by the motor as the member passes through the substance.

20. A method as claimed in claim 14 in which the member has at least one blade extending from an axis and having a profile with an increasing pitch angle with respect to the axial direction with increasing radial distance from the axis.

21. A method as claimed in claim 20 including driving the at least one blade in the opposite direction to that dictated by the pitch angle.

22. A method as claimed in claim 20 in which the at least one blade is adapted to pass through the substance with substantially zero slip at given axial and rotary speeds.

23. A method as claimed in claim 14 in which the rheometric assessment is derived from the monitored parameter once a predetermined force is reached.

24. A rheometer comprising:
a vessel for a substance to be rheometrically assessed;
a blade member;
drive means for rotating and axially moving the blade member through the substance in the vessel;
means for monitoring a parameter indicative of the axial resistive force alone of the substance to the passage of the member through the substance; and
means for deriving a rheometric assessment of the substance from the monitored parameter, including means for calculating the work done in axially moving the member.

25. A rheometer as claimed in claim 24, including means for measuring axial distance travelled by the member while the parameter is monitored.

26. A rheometer comprising:
a vessel for a substance to be rheometrically assessed;
a blade member;
drive means for rotating and axially moving the blade member through the substance in the vessel, including an electric motor arranged to drive one of the blade member and the vessel to achieve relative motion between them;
means for monitoring a parameter indicative of the axial resistive force alone of the substance to the passage of the member through the substance, including current sensing means arranged to monitor the current drawn by the motor; and
means for deriving a rheometric assessment of the substance from the monitored parameter.

27. A method of rheometric analysis of a substance comprising:
preparing a substance for analysis in a vessel;
rotating and axially driving a blade member through the substance to shear it;
monitoring a parameter indicative of the axial resistive force alone of the substance to movement of the member through the substance; and
deriving a rheometric assessment of the substance from the monitored parameter, including calculating the work done in axially moving the member.

28. A method as claimed in claim 27 including measuring an axial distance travelled by the member while the parameter is monitored.

29. A method of rheometric analysis of a substance comprising:
preparing a substance for analysis in a vessel;
rotating and axially driving a blade member through the substance to shear it, an electric motor arranged to move the member relative to the vessel;
monitoring a parameter indicative of the axial resistive force alone of the substance to movement of the member through the substance, including sensing the current drawn by the motor as the member passes through the substance; and
deriving a rheometric assessment of the substance from the monitored parameter.

30. A method of rheometric analysis of a substance comprising:
preparing a substance for analysis in a vessel;
rotating and axially driving a blade member through the substance to shear it;
monitoring a parameter indicative of the axial resistive force alone of the substance to movement of the member through the substance; and
deriving a rheometric assessment of the substance from the monitored parameter, once a predetermined force is reached.

* * * * *